United States Patent [19]
van Eekelen et al.

[11] Patent Number: 5,336,611
[45] Date of Patent: Aug. 9, 1994

[54] PB92 SERINE PROTEASE MUTEINS AND THEIR USE IN DETERGENTS

[75] Inventors: Christiaan A. G. van Eekelen, Bergschenhoek; Leonardus J. S. M. Mulleners, SV Rijen; Johannes C. Van Der Laan, Amsterdam; Onno Misset, Delft; Roelck A. Cuperus, Amsterdam; Johan H. A. Lensink, Delft, all of Netherlands

[73] Assignee: Gist-brocades N.V., Delft, Netherlands

[21] Appl. No.: 427,103

[22] PCT Filed: Feb. 13, 1989

[86] PCT No.: PCT/NL89/00005

§ 371 Date: Oct. 11, 1989

§ 102(e) Date: Oct. 11, 1989

[87] PCT Pub. No.: WO89/07642

PCT Pub. Date: Aug. 24, 1989

[30] Foreign Application Priority Data

Feb. 11, 1988 [EP] European Pat. Off. ........ 88200255.3

[51] Int. Cl.⁵ .................... C12N 9/54; C11D 3/386
[52] U.S. Cl. .............................. 435/221; 252/174.12
[58] Field of Search ................ 435/221; 252/174.12

[56] References Cited

U.S. PATENT DOCUMENTS

| | | | |
|---|---|---|---|
| 3,790,482 | 2/1974 | Jones et al. | 252/525 |
| 4,511,490 | 8/1985 | Stanislowski et al. | 435/219 |
| 4,760,025 | 7/1988 | Estell et al. | 435/222 |
| 4,990,452 | 2/1991 | Bryan et al. | 435/222 |

FOREIGN PATENT DOCUMENTS

| | | |
|---|---|---|
| 130756 | 1/1985 | European Pat. Off. . |
| 251446 | 1/1988 | European Pat. Off. . |
| 283075 | 2/1988 | European Pat. Off. . |
| 2292042 | 6/1976 | France . |
| WO87/04461 | 7/1987 | PCT Int'l Appl. . |
| WO87/05050 | 8/1987 | PCT Int'l Appl. . |
| WO88/08028 | 10/1988 | PCT Int'l Appl. . |
| WO88/08033 | 10/1988 | PCT Int'l Appl. . |
| WO89/06279 | 7/1989 | PCT Int'l Appl. . |

OTHER PUBLICATIONS

Chemical Abstracts vol. 110, 1989, p. 125, Abstract 156553B of the article "Protein-Engineering of the High Alkaline Detergent Protease Maxacal" *Comm Jorn Com. Esp. Detrg.* (1988) 19:257-66, by Vaneee, et al.

"The Engineering of Binding Affinity at Metal Ion Binding Sites for the Stabilization of Protein: Subtilisin as a Test Case": *Biochemistry* (1988) 27:8311-8317, by Pantoliano et al.

"Cloning of Protease Gene Produced by Heat-Resistant Alkalinic *Bacillus, E. coli*" *Korean J. Appl. Microbiol. Bioeng.* (1986) 14:517.

"Engineering Enzyme Specificity by Substrate-Assisted Catalysis" *Science* (1987) 237:394-399 by Carter & Wells.

Reeck et al, (1987) *Cell,* 50, 667.

Boswell et al, (1988) in "Computational Molecular Biology", pp. 161-178, Lesk, Ed., Oxford Press, Oxford.

Meloun et al. (1985) *FEBS Lett.,* 183(2), 195-199.

*Primary Examiner*—Douglas W. Robinson
*Assistant Examiner*—Jon P. Weber
*Attorney, Agent, or Firm*—Barbara Rae-Venter

[57] ABSTRACT

New proteolytic enzymes are provided exhibiting improved properties for application in detergents, especially laundry detergents. These enzymes are obtained by expression of a gene encoding a proteolytic enzyme having an amino acid sequence which differs at least in one amino acid from the wild type enzyme. Preferred enzymes are certain mutants derived from the serine protease of Bacillus nov. spec. PB92.

8 Claims, 8 Drawing Sheets

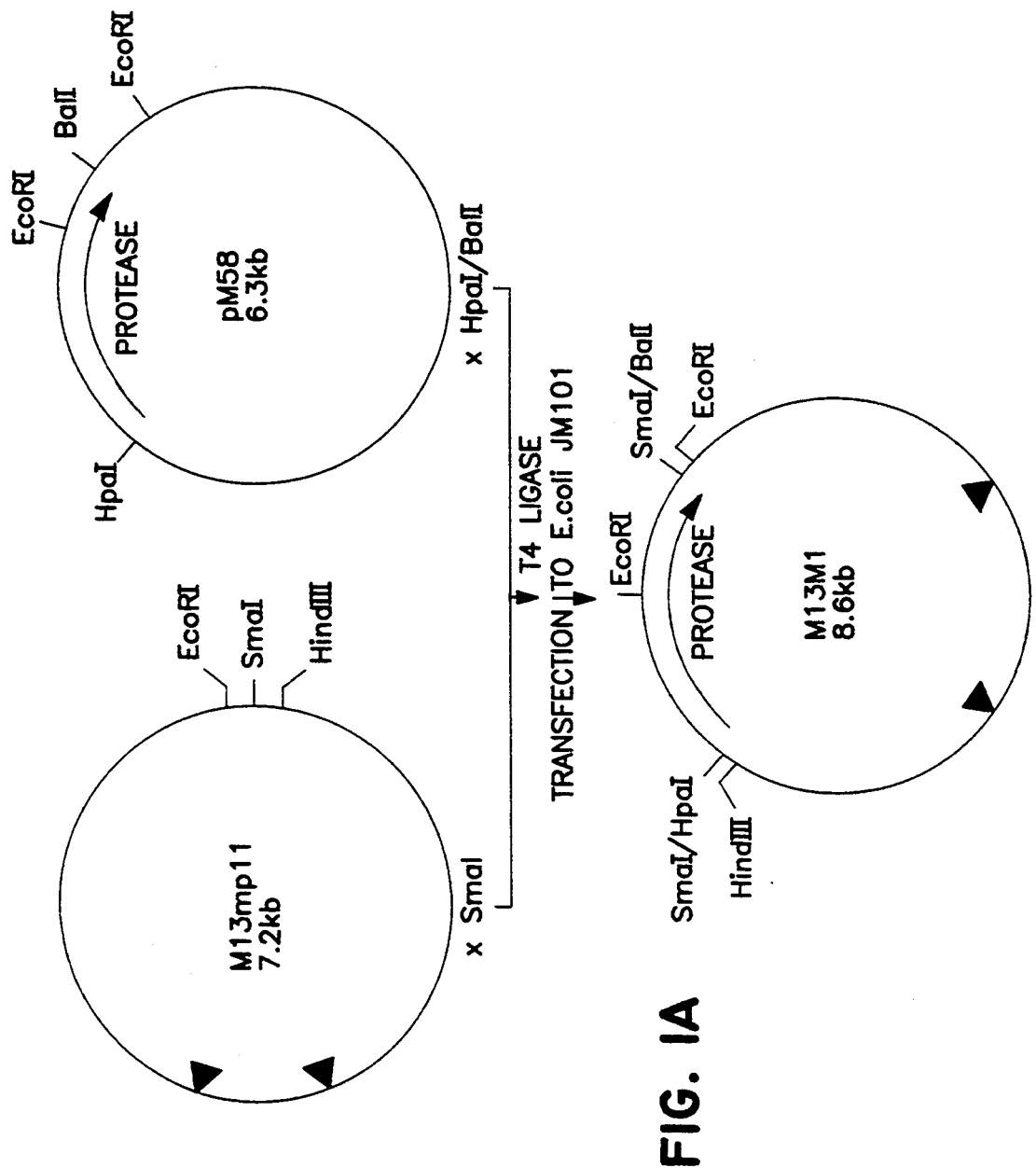
FIG. IA

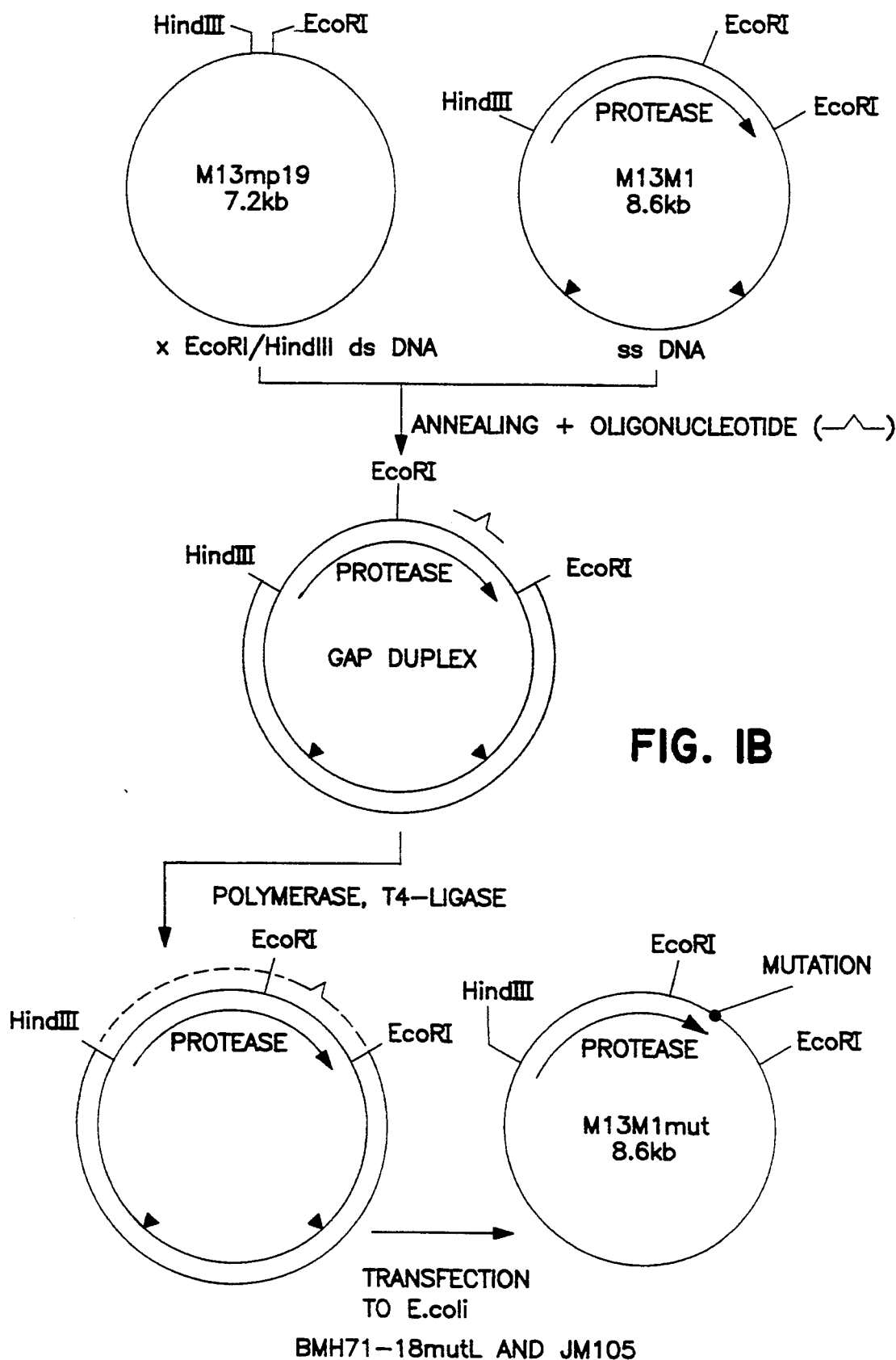
FIG. IB

```
                                        ┌──── Pre
                                        │ -100
────────────────────────ATGAAGAAACCGTTGGGGAAAATTGTCGCAAGC
                        M  K  K  P  L  G  K  I  V  A  S
                                                        ┌──── Pro
                    -90                                 │
ACCGCACTACTCATTTCTGTTGCTTTTAGTTCATCGATCGCATCGGCTGCTGAAGAAGCA
 T  A  L  L  I  S  V  A  F  S  S  S  I  A  S  A  A  E  E  A

-70
AAAGAAAAATATTTAATTGGCTTTAATGAGCAGGAAGCTGTCAGTGAGTTTGTAGAACAA
 K  E  K  Y  L  I  G  F  N  E  Q  E  A  V  S  E  F  V  E  Q

-50
GTAGAGGCAAATGACGAGGTCGCCATTCTCTCTGAGGAAGAGGAAGTCGAAATTGAATTG
 V  E  A  N  D  E  V  A  I  L  S  E  E  E  E  V  E  I  E  L

-30
CTTCATGAATTTGAAACGATTCCTGTTTTATCCGTTGAGTTAAGCCCAGAAGATGTGGAC
 L  H  E  F  E  T  I  P  V  L  S  V  E  L  S  P  E  D  V  D

-10
GCGCTTGAACTCGATCCAGCGATTTCTTATATTGAAGAGGATGCAGAAGTAACGACAATG
 A  L  E  L  D  P  A  I  S  Y  I  E  E  D  A  E  V  T  T  M
┌──── Mature
│ +1                 10                      20
GCGCAATCAGTGCCATGGGGAATTAGCCGTGTGCAAGCCCCAGCTGCCCATAACCGTGGA
 A  Q  S  V  P  W  G  I  S  R  V  Q  A  P  A  A  H  N  R  G 30                       40
TTGACAGGTTCTGGTGTAAAAGTTGCTGTCCTCGATACAGGTATTTCCACTCATCCAGAC
 L  T  G  S  G  V  K  V  A  V  L  D  T  G  I  S  T  H  P  D 50                       60
TTAAATATTCGTGGTGGCGCTAGCTTTGTACCAGGGGAACCATCCACTCAAGATGGGAAT
 L  N  I  R  G  G  A  S  F  V  P  G  E  P  S  T  Q  D  G  N 70                       80
GGGCATGGCACGCATGTGGCTGGGACGATTGCTGCTTTAAACAATTCGATTGGCGTTCTT
 G  H  G  T  H  V  A  G  T  I  A  A  L  N  N  S  I  G  V  L
```

FIG. 4A

```
                                      90                            100
GGCGTAGCACCGAACGCGGAACTATACGCTGTTAAAGTATTAGGGGCGAGCGGTTCAGGT
 G  V  A  P  N  A  E  L  Y  A  V  K  V  L  G  A  S  G  S  G 110                            120
TCGGTCAGCTCGATTGCCCAAGGATTGGAATGGGCAGGGAACAATGGCATGCACGTTGCT
 S  V  S  S  I  A  Q  G  L  E  W  A  G  N  N  G  M  H  V  A 130                            140
AATTTGAGTTTAGGAAGCCCTTCGCCAAGTGCCACACTTGAGCAAGCTGTTAATAGCGCG
 N  L  S  L  G  S  P  S  P  S  A  T  L  E  Q  A  V  N  S  A 150                            160
ACTTCTAGAGGCGTTCTTGTTGTAGCGGCATCTGGGAATTCAGGTGCAGGCTCAATCAGC
 T  S  R  G  V  L  V  V  A  A  S  G  N  S  G  A  G  S  I  S 170                            180
TATCCGGCCCGTTATGCGAACGCAATGGCAGTCGGAGCTACTGACCAAAACAACAACCGC
 Y  P  A  R  Y  A  N  A  M  A  V  G  A  T  D  Q  N  N  N  R 190                            200
GCCAGCTTTTCACAGTATGGCGCAGGGCTTGACATTGTCGCACCAGGTGTAAACGTGCAG
 A  S  F  S  Q  Y  G  A  G  L  D  I  V  A  P  G  V  N  V  Q 210                            220
AGCACATACCCAGGTTCAACGTATGCCAGCTTAAACGGTACATCGATGGCTACTCCTCAT
 S  T  Y  P  G  S  T  Y  A  S  L  N  G  T  S  M  A  T  P  H 230                            240
GTTGCAGGTGCAGCAGCCCTTGTTAAACAAAAGAACCCATCTTGGTCCAATGTACAAATC
 V  A  G  A  A  A  L  V  K  Q  K  N  P  S  W  S  N  V  Q  I 250                            260
CGCAATCATCTAAAGAATACGGCAACGAGCTTGGGAAGCACGAACTTGTATGGAAGCGGA
 R  N  H  L  K  N  T  A  T  S  L  G  S  T  N  L  Y  G  S  G

270
CTTGTCAATGCAGAAGCGGCAACACGCTAA
 L  V  N  A  E  A  A  T  R End
```

FIG. 4B

PB92 SERINE PROTEASE MUTEINS AND THEIR USE IN DETERGENTS

INTRODUCTION

1. Technical Field

The present invention relates to novel proteolytic enzymes having improved properties for use in detergents. These properties include improved stain removing ability in laundry detergent washing compositions, improved stability in laundry detergents upon storage and improved stability in suds prepared from the detergents.

2. Background of the Invention

Use of enzymatic additives, in particular proteolytic enzymes, in detergent compositions to enable removal of protein based soilings has been amply documented. See for example the published European Patent Applications (EP-A-) 0220921 and 0232269, U.S. Pat. Nos. 4,480,037 and Re 30,602, and the article "Production of Microbial Enzymes", Microbial Technology, vol. 1 (1979) 281-311, Academic Press.

Detergent compositions may be in a powder, liquid or paste form. They contain one or more anionic, non-ionic, cationic, zwitterionic or amphoteric compounds as the detergent active material. Such compounds are described at length in "Surface Active Agents" Vol II by Schwartz, Perry and Berch, Interscience Publishers (1958). Furthermore, they may include sequestering agents, stabilizing compounds, fragrance compounds and in some cases oxidizing agents, usually called bleaches. Detergent compositions are applied for hard surface cleaning, toilet cleaning, dish washing (either automatic or by hand) and laundry cleaning.

Laundry detergents are generally divided into two major types, liquids and powders. Liquid laundry detergents have high concentrations of surfactants, neutral to moderately alkaline pH and generally do not contain bleaching agents. Powder detergents mostly have high alkalinity (sud pH 9-11); they contain sequestering agents like sodium tripolyphosphate and, depending on the washing habits of the countries where they are sold, they may or may not contain bleaching agents.

Enzymes currently used in detergent compositions are added in liquid suspension, sol or granulate form. For example, in powder detergents the proteolytic enzymes are generally present in an encapsulated form such as prills (e.g. of Maxatase ® and Maxacal ®) or granulates (e.g. of Savinase ® and Alcalase ®). Maxatase and Maxacal are marketed by International Bio-Synthetics B.V. (Rijswijk, The Netherlands), Savinase and Alcalase by NOVO Industri A/S (Bagsvaerd, Denmark). In liquid laundry detergents, enzymes are mostly present in solution.

Proteolytic enzymes are generally difficult to combine with detergent compositions. They must be stable and active during application, for example in removing proteinaceous stains from textile during washing at temperatures ranging from about 10° C. to over 60° C. Furthermore they must be stable for prolonged periods of time during storage in the detergent product. Consequently, enzymes have to be stable and functional in the presence of sequestering agents, surfactants, high alkalinity, in some cases bleaching agents, and elevated temperature. As there exist neither universal laundry detergents nor universal washing conditions (pH, temperature, sud-concentration, water hardness) that are used all over the world, the demands on enzymes may vary based on the type of detergent in which they are used and on the washing conditions.

The conditions governing the stability of enzymes in powder detergents are generally not optimal. For example, during storage of enzyme preparations in powder detergents, despite the apparent physical separation of the enzyme from the detergent matrix by encapsulation of the enzyme, oxidizing agents from the detergent affect the protease and reduce its activity. Another cause of instability of the enzyme in powder detergents during storage, is autodigestion, especially at high relative humidities.

Moreover, oxidizing agents often present in powder detergents have an important drawback on stain removing efficiency during application in laundry cleaning by way of fixation of proteinaceous stains to the fabric. Additionally, these oxidizing agents and other detergent components, like sequestering agents, reduce the efficiency of the protease in stain removal also during the washing process.

In liquid detergents an important problem is rapid inactivation of enzymes, especially at elevated temperatures. As the enzymes are present in the detergent product in solution, this inactivation already takes place in the detergent product during normal storage conditions and considerably reduces the activity of the enzymes before the product is actually used. In particular anionic surfactants, such as alkyl sulfates, in combination with water and builders, tend to denature the enzyme irreversibly and render it inactive or susceptible to proteolytic degradation.

Partial solutions for stability problems relating to enzymes in liquid detergents are found in adaptations of the liquid detergent formulation such as the use of stabilizing agents reduce inactivation of the enzymes. See EP-A-0126505 and EP-A-0199405, U.S. Pat. No. 4,318,818 and U.K. patent application No. 2178055A.

Another approach to ensure stability of enzymes in liquid detergents is described in EP-A-0238216, where physical separation between the enzyme molecules and the hostile liquid detergent matrix is achieved by formulation technology. In powder detergents alternative encapsulates have been proposed, see for example EP-A-0170360.

In the aforegoing the conditions are summarized which proteolytic detergent enzymes have to meet for optimal functioning, as well as the limitations of the currently available enzymes for use in detergent compositions. Despite the efforts to ensure enzyme stability in detergent compositions, substantial activity loss is still encountered under normal conditions of storage and application.

Identification and isolation of new enzymes for a certain intended application, such as use in detergents, can be performed in several ways. One way is screening for organisms or microorganisms that display the desired enzymatic activity, isolating and purifying the enzyme from the (micro)organism or from a culture supernatant of said (micro)organism, determining its biochemical properties and checking whether these biochemical properties meet the demands for the application. If the identified enzyme cannot be obtained from its natural producing organism, recombinant DNA techniques may be used to isolate the gene encoding the enzyme, express the gene in another organism, isolate and purify the expressed enzyme and test whether it is suitable for the intended application.

Another way of obtaining new enzymes for an intended application is the modification of existing enzymes. This can be achieved inter alia by chemical modification methods (see I. Svendsen, Carlsberg Res. Commun. 44 (1976), 237–291). In general these methods are too nonspecific in that they modify all accessible residues with common side chains, or they are dependent on the presence of suitable amino acids to be modified, and are often unable to modify amino acids difficult to reach, unless the enzyme molecule is unfolded. Therefore, the enzyme modification method through mutagenesis of the encoding gene is thought to be superior.

Mutagenesis can be achieved either by random mutagenesis or by site-directed mutagenesis. Random mutagenesis, by treating a whole microorganism with a chemical mutagen or with mutagenizing radiation may of course result in modified enzymes. In this case strong selection protocols must be available to search for the extremely rare mutants having the desired properties. A higher probability of isolating mutant enzymes by random mutagenesis can be achieved, after cloning the encoding gene, by mutagenizing it in vitro or in vivo and expressing the encoded enzyme by recloning of the mutated gene in a suitable host cell. Also in this case suitable biological selection protocols must be available in order to select the desired mutant enzymes, see International patent application WO 87/05050. These biological selection protocols do not specifically select enzymes suited for application in detergents.

The most specific way of obtaining modified enzymes is by site-directed mutagenesis, enabling specific substitution of one or more amino acids by any other desired amino acid. EP-A-0130756 exemplifies the use of this technique for generating mutant protease genes which can be expressed to give modified proteolytic enzymes.

Recently the potential of oligonucleotide mediated site-directed mutagenesis has been demonstrated through the use of mutagenic oligonucleotides synthesized to contain mixtures of bases at several positions within a target sequence. This allows a number of different mutations to be introduced at a specific part of a DNA sequence by using a single synthetic oligonucleotide preparation as exemplified by (Hui et al., EMBO J. 3 (1984) 623–629, Matteucci et al., Nucl. Acids Res. 11 (1983) 3113–3121, Murphy et al., Nucl. Acids Res. 11 (1983) 7695–7700, Wells et al., Gene 34 (1985) 315–323, Hutchinson et al., Proc. Natl. Acad. Sci. USA 83 (1986) 710–714 and F. M. Ausubel, Current Protocols in Molecular Biology 1987–1988, Greene Publishers Association and Wiley, Interscience, 1987.

Stauffer et al., J. Biol. Chem. 244 (1969) 5333–5338 has already found that the methionine at position 221 in Carlsberg subtilisin is oxidized by $H_2O_2$ to methionine sulfoxide and is responsible for a dramatic decrease of the activity.

As a result of both the methods of random and site-directed mutagenesis for generating modified enzymes, mutants derived from the serine protease of *Bacillus amyloliquefaciens*, also called "subtilisin BPN'", were isolated and characterized. In WO 87/05050 a mutant subtilisin BPN' is disclosed with enhanced thermal stability. In EP-A-0130756 is described that site directed mutagenesis of methionine at position 222 in subtilisin BPN' by all 19 possible amino acids, using the so-called "cassette mutagenesis" method, may result in enzymes resistant towards oxidation by $H_2O_2$. In the latter case, however, most mutants had low proteolytic activity.

The best mutants found were M222A and M222S, which had specific activities of 53% and 35%, respectively, compared to the native subtilisin BPN', see Estell et al., J. Biol. Chem. 260 (1985) 6518–6521.

Prior work on generating modified proteases shows that subtilisin BPN' mutants with altered stability properties and altered kinetic properties can be obtained; see the literature referred to above and other references, for example Rao et al., Nature 328 (1987) 551–554, Bryan et al., Proteins 1 (1986) 326–334, Cunningham and Wells, Protein Engineering 1 (1987) 319–325 Russell et al., J. Mol. Biol. 193 (1987) 803–819, Katz and Kossiakoff, J. Biol. Chem. 261 (1986) 15480–15485, and the reviews by Shaw, Biochem. J. 246 (1987) 1–17 and Gait et al., Protein Engineering 1 (1987) 267–274. However, none of these references have led to the industrial production of proteolytic enzymes with improved wash performance and stability in laundry detergents. None of the modified proteases have been shown to be of commercial value so far and superior to presently used detergent enzymes under relevant application conditions.

SUMMARY OF THE INVENTION

In one aspect the present invention provides new mutant proteolytic enzymes, obtained by expression of genes encoding said enzymes having amino acid sequences which differ at least in one amino acid from the corresponding wild-type enzymes. These mutant enzymes exhibit improved properties for application in detergents, especially laundry detergents. A preferred embodiment of the invention is constituted by mutants of PB92 serine protease.

In another aspect the invention provides new enzymatic detergents, comprising a proteolytic enzyme product which contains at least one of such new mutant proteolytic enzymes.

In a further aspect this invention provides a test system, which enables efficient selection of mutant proteolytic enzymes with improved properties for application in laundry detergents out of dozens of enzymes. Such enzymes are produced by expression of mutagenized protease genes.

These and other aspects of the invention will be further outlined in the detailed description hereinafter.

BRIEF DESCRIPTION OF THE DRAWINGS

FIG. 1A shows the construction of the mutation vector containing the PB92 protease gene.

FIG. 1B shows schematically the mutation procedure used.

FIGS. 4A and B show the nucleotide sequence of the PB92 protease gene and the amino acid sequence of the encoded precursor enzyme.

DETAILED DESCRIPTION OF THE INVENTION

Figure 1C:
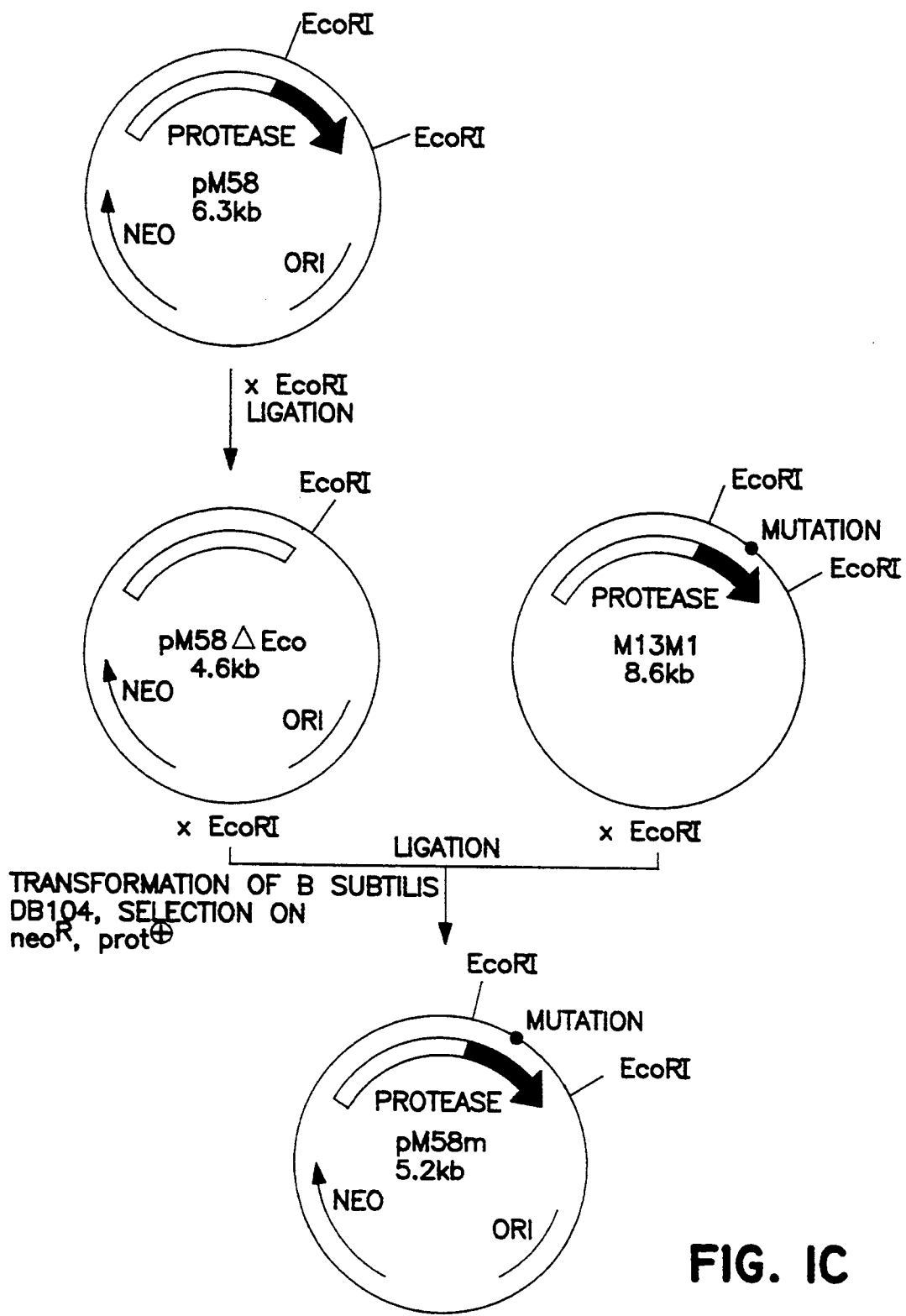
FIG. 1C shows the construction of an expression vector containing a mutant PB92 protease gene.

By the term "having improved properties" as used in this specification in connection with "mutant proteolytic enzymes" we mean proteolytic enzymes with improved wash performance or improved stability with retained wash performance, relative to the corresponding wild-type protease.

The term "wash performance" of mutant proteolytic enzymes is defined in this specification as the contribution of a mutant proteolytic enzyme to laundry cleaning additional to the effect of the detergent composition without enzyme under relevant washing conditions.

The term "relevant washing conditions" is used to indicate the conditions, particularly washing temperature, time, washing mechanics, sud concentration, type of detergent and water hardness, actually used in households in a detergent market segment.

The term "improved wash performance" is used to indicate that a better end result is obtained in stain removal under "relevant washing conditions" or that less mutant proteolytic enzyme, on weight basis, is needed to obtain the same end result relative to the corresponding wild-type enzyme.

The term "retained wash performance" is used to indicate that the wash performance of a mutant proteolytic enzyme, on weight basis, is at least 80% relative to the corresponding wild-type protease under "relevant washing conditions".

The term "improved stability" is used to indicate better stability of mutant proteolytic enzymes in laundry detergents during storage and/or their stability in the sud, which includes stability against oxidizing agents, sequestering agents, autolysis, surfactants and high alkalinity, relative to the corresponding wild-type enzyme.

Biochemical properties determined under well defined laboratory conditions are not reliable parameters to predict the performance of a particular detergent protease under desired and specified application conditions. These parameters include kinetic data measured on well defined substrates, such as proteins like casein, dimethylcasein and hemoglobin, or substituted oligopeptide substrates like sAAPFpNA (succinyl-L-alanyl-L-alanyl-L-prolyl-L-phenyl-alanyl-paranitroanilide). Apparently other features of the proteases determine their efficiency in laundry cleaning.

The present invention is based on the finding that although methods for introducing amino acid changes into proteins are available, which can effect major changes in their biochemical characteristics, prediction of the effect of specific mutations under actual application conditions is still very poor or even impossible.

According to the invention a method has now been found, after extensive research and experimentation, which combines the preparation of mutant proteases with an efficient selection procedure on the performance of these proteases. It is surprising that relatively large numbers of enzymes can be efficiently screened for performance in this way.

The test system according to the invention is based on the removal of protease sensitive stains from test swatches in a launderometer or tergotometer, imitating relevant washing conditions. Suitable test swatches are, for example, the commercially available EMPA (Eidgenössische Material Prüfungs und Versuch Anstalt, St. Gallen, Switzerland) swatches, artificially soiled with proteinaceous stains. Relevant stains on swatches for testing proteases include blood, grass, chocolate stains, and other proteinaceous stains.

Moreover, in this test system other relevant factors, such as detergent composition, sud concentration, water hardness, washing mechanics, time, pH and temperature, can be controlled in such a way that conditions typical for household application in a certain market segment can be imitated.

Wash performance of proteases is conveniently measured by their ability to remove certain representative stains under appropriate test conditions. This ability can be suitably determined by reflectance measurements on the test cloths, after washing with and without enzymes in a launderometer or tergotometer. The laboratory application test system according to the invention is representative for household application when used on proteolytic enzymes modified through DNA mutagenesis.

Accordingly, the invention enables the testing of large amounts of different enzymes and the selection of those enzymes which are particularly suitable for a specific type of detergent application. In this way "tailor made" enzymes for specific application conditions can be easily selected.

Some bacterial serine proteases are referred to as subtilisins. Subtilisins comprise the serine proteases of *Bacillus subtilis*, *Bacillus amyloliquefaciens* ("subtilisin BPN'"), and *Bacillus licheniformis* ("subtilisin Carlsberg"). See the review by Markland and Smith (1971) in "The Enzymes" (Boyer, ed.) vol. 3, 561–608, Academic Press, New York. Bacillus strains such as alkalophilic Bacillus strains produce other proteases. Examples of the latter category are the serine proteases in Maxacal, hereinafter also called PB92 protease (from Bacillus nov. spec. PB92), and in Savinase, mentioned before.

The amino acid sequence of the PB92 protease is shown in FIG. 4. The mature protease consists of 269 amino acids representing a molecular weight of about 27000 D and has an iso-electric point in the high alkaline range. The activity on protein substrate of PB92 protease is expressed in Alkaline Delft Units (ADU). The activity in ADU is determined according to the method described in British Patent Specification No. 1,353,317 except that the pH was changed from 8.5 to 10.0. Purified PB92 protease has an activity of 21,000 ADU per mg. The turnover number ($k_{cat}$) measured on casein is 90 sec$^{-1}$ molecule $^{-1a}$.

The specific activity of purified preparations of subtilisin Carlsberg (Delange and Smith, J. Biol. Chem. 243 (1968) 2184), amounts to 10,000 ADU/mg and of subtilisin BPN' (Matsubara et al., J. Biol. Chem. 240 (1965) 1125) to 7,000 ADU/mg. Besides the above-mentioned parameters such as specific activity and turnover number ($k_{cat}$), PB92 protease distinguishes itself from proteases like Carlsberg subtilisin, subtilisin BPN' and other proteases formulated in detergents (e.g. Maxatase and Alcalase) in having a high positive charge, which can be visualized by gel-electrophoresis of the native protein as described hereinafter in Experimental Section 4.

Since the PB92 protease is active in stain removing at alkaline pH-values, it is commonly used as a detergent additive, together with detergent ingredients such as surfactants, builders and oxidizing agents. The latter agents are mostly used in powder form. PB92 protease has a high stain removing efficiency as compared to other proteases, such as the aforementioned subtilisins. This means that less PB92 protease is needed to get the same wash performance.

Sensitivity to oxidation is an important drawback of the PB92 protease and all other known serine proteases used for application in detergents (see also Stauffer et al., J. Biol. Chem. 244 (1969) 5333–5338; Estell et al., J. Biol. Chem. 263 (1985) 6518–6521). Oxidation of PB92 protease by either $H_2O_2$ or peracids generated by the activator system, containing perborate-tetrahydrate and TAED, creates an enzyme with a specific activity of 50% and 10%, respectively, on ADU/mg, compared to non-oxidized PB92 protease (see Experimental Section 7 and Example 1).

The method according to the present invention is very suitable for the production, screening and selection of mutant proteolytic enzymes which are derived from naturally produced bacterial serine proteases. Such mutants are, for example, those encoded by a gene derived from a wild-type gene of an alkalophilic Bacillus strain, and, preferably PB92. Also mutants derived from the alkalophilic Bacillus serine protease savinase are suitable. The method can further be advantageously used for the selection of modified proteases derived from proteases other than the serine proteases from alkalophilic Bacillus strains PB92. For example, the genes encoding the serine proteases of *Bacillus subtilis*, *Bacillus amyloliquefaciens* and *Bacillus licheniformis* are known and can be used as target for mutagenesis. It will be clear that either oligonucleotide aided site directed mutagenesis or region directed random mutagenesis can be used or any other suitable method for efficiently generating mutations in the protease gene.

The method for selecting mutant proteolytic enzymes according to the present invention (which includes the production and screening) comprises the following steps: mutagenizing a cloned gene encoding a proteolytic enzyme of interest or a fragment thereof; isolating the obtained mutant protease gene or genes; introducing said mutant protease gene or genes, preferably on a suitable vector, into a suitable host strain for expression and production; recovering the produced mutant protease; and identifying those mutant proteases having improved properties for application in detergents.

Suitable host strains for production of mutant proteases include transformable microorganisms in which expression of the protease can be achieved. Specifically host strains of the same species or genus from which the protease is derived, are suitable, such as a Bacillus strain, preferably an alkalophilic Bacillus strain and most preferably Bacillus nov. spec. PB92 or a mutant thereof having substantially the same properties. Also *B. subtilis*, *B. licheniformis* and *B. amyloliquefaciens* strains are among the preferred strains. Other suitable and preferred host strains include those strains which are substantially incapable of producing extracellular proteolytic enzymes prior to the transformation with a mutant gene. Of particular interest are protease deficient Bacillus host strains, such as a protease deficient derivative of Bacillus nov. spec. PB92. Expression of the proteases is obtained by using expression signals that function in the selected host organism. Expression signals include sequences of DNA regulating transcription and translation of the protease genes. Proper vectors are able to replicate at sufficiently high copy numbers in the host strain of choice or enable stable maintenance of the protease gene in the host strain by chromosomal integration.

The mutant proteolytic enzymes according to the invention are prepared by cultivating, under appropriate fermentation conditions, a transformed host strain comprising the desired mutant proteolytic gene or genes, and recovering the produced enzymes.

Preferably, the proteases being expressed are secreted into the culture medium, which facilitates their recovery, or in the case of gram negative bacterial host strains into the periplasmic space. For secretion a suitable amino-terminal signal sequence is employed, preferably the signal sequence encoded by the original gene if this is functional in the host strain of choice.

According to an aspect of the invention suitable wash performance tests can be developed which are representative for any relevant household washing conditions in the market. For example, a suitable test was developed for the heavy duty European powder detergent market, in which powdered built detergents are used which may or may not contain bleaching agents at sud concentrations ranging from 1-10 g detergent/l at 10°-20° GH (German Hardness) used at temperatures between 25°-80° C. More specifically a powdered built detergent was used containing TAED and perborate at a sud concentration of 4, 7 or 10 g detergent/l at 15° GH at 40° C.

Also tests are provided which are representative for washing with liquid detergents. These detergents are commonly used at sud concentrations ranging from 1.5-5 g detergent/l at 5°-15° GH at temperatures between 15° and 40° C. More specifically non-bleach liquid detergent compositions were used at a sud concentration of 1.5 g detergent/l, 5° GH, at 25° C. and 40° C., representing U.S. liquid detergent conditions, and a sud concentration of 5 g detergent/l 15° GH at 40° C., representing European liquid detergent conditions.

Proper performance assays can be developed for other conditions met in the market. Test swatches soiled with protease sensitive stains, particularly swatches soiled with blood, grass, chocolate stains and other proteinaceous stains, more specifically the EMPA test swatches 116 and 117, are employed in representative wash performance tests.

The properties of the naturally occurring or naturally mutated detergent proteases may be enhanced by introducing a variety of mutations in the enzyme. For the most part, the mutations will be substitutions, either conservative or non-conservative, but deletions and insertions may also find use.

For conservative substitutions the following table may be employed:

| Aliphatic | |
|---|---|
| neutral | |
| non-polar | G, A, P |
| | L, I, V |
| polar | C, M, S, T, |
| | N, Q |
| charged | |
| anionic | D, E |
| cationic | K, R |
| Aromatic | F, H, W, Y | where any amino acid may be substituted with any other amino acid in the same category, particularly on the same line. In addition, the polar amino acids N, Q may substitute or be substituted for by the charged amino acids. For the purpose of the subject invention, substitutions resulting in increased anionic character of the protease, particularly at sites not directly involved with the active site are of particular interest.

Regions of particular interest for mutation are those amino acids within 4 Å distance from the inhibitor molecule Eglin C, when Eglin C is bound to the active site.

The following numbering is based on PB92 protease, but the considerations are relevant to other serine proteases having a substantially homologous structure, particularly those having greater than about 70% homology, more particularly, having greater than about 90% homology. These positions will be 32, 33, 48–54, 58–62, 94–107, 116, 123–133, 150, 152–156, 158–161, 164, 169, 175–186, 197, 198, 203–216, most of these positions being available for direct interaction with a proteinaceous substrate. Usually, the positions 32, 62, 153 and 215 will not be substituted, since mutations at these sites tends to degrade wash performance.

Positions for substitution of particular interest include 60, 62, 94, 97–102, 105, 116, 123–128, 150, 152, 153, 160, 183, 203, 211, 212, and 213–216. At some positions there will be an intent to change an unstable amino acid, e.g. methionine to an oxidatively more stable amino acid, e.g. threonine, while maintaining the general conformation and volume of the amino acid at that site. In other situations, it is found that by replacing the natural amino acid with almost any other amino acid, improved results may be obtained, particularly replacing the hydroxylated amino acids, S, T, with a polar or non-polar amino acid, or even an aromatic amino acid.

Substitutions of particular interest include:

| | |
|---|---|
| G116 | I, V, L |
| S126 | any amino acid |
| P127 | any amino acid |
| S128 | any amino acid |
| S160 | anionic or neutral aliphatic or R |
| A166 | charged, particularly anionic |
| M169 | neutral aliphatic, preferably non-polar |
| N212 | anionic |
| M216 | aliphatic polar, particularly S, T, N, Q |

Surprisingly, while many of the mutations result in lower specific activity of the protease with common substrates, wash performance is comparable to or enhanced in relation to the natural enzyme and in many cases storage stability is improved.

The wash performance of some of the PB92 mutant proteases, when expressed as the inverse of the relative amount of enzyme necessary to achieve the same effect as with the native proteases×100%, is increased to more than 120%, in certain cases even to more than 180%.

According to another aspect of the invention PB92 protease mutants are provided which show a better storage stability in a powder detergent composition containing bleaching agent than the native PB92 protease, while retaining their wash performance. Examples of such mutants are M216S and M216Q and mutants having at least one of these mutations besides mutations on other sites.

According to still another aspect of the invention it was surprisingly found that in a liquid laundry detergent composition (containing no oxidizing agents) the mutant PB92-proteases M216S, M216Q, S160D and N212D retain their activity better than PB92 protease. Of these mutants, M216S and M216Q have retained wash performance and S160D and N212D improved wash performance. The improvement in storage stability in the tested liquid detergent is most pronounced for the S160D and M216Q mutants.

It is also possible to combine several mutations that increase the stability of a protease in detergent compositions. Several mutations that positively influence the wash performance of the same protease can be combined into a single mutant protease gene enabling production of possibly even further improved proteases, for example [S126M, P127A, S128G, S160D] and [G116V, S126N, P127S, S128A, S160D]. New protease mutants can be made by combining the good wash performance properties of, for example, N212D and S160D with the stability properties of, for example, M216S or M216Q. The [S160D, M216S] mutant, for example, shows improved wash performance and better storage stability.

Useful mutants may also be made by combining any of the mutations or sets of mutations described in this specification. Besides, it is possible to combine useful mutations as disclosed herein with mutations at other sites, which may or may not cause a substantial change in the properties of the enzyme.

Preferred embodiments of the present invention are the following PB92 protease mutants: [M216S]; [M216Q]; N212D]; [S160D]; [S160G, N212D]; [S160D, M216Q]; [S160D, M216S]; [A166D, M169I]; [G116V, S126V, P127E, S128K]; [G116V, S126G, P127Q, S128I]; [G116V, S126L, P127N, S128V]; [G116V, S126L, P127Q, S128A]; [G116V, S126V, P127M]; [G116V, S126H, P127Y]; [G116V, S126R, P127S, S128P]; [G116V, S126F, P127Q]; [G116V, S126F, P127L, S128T]; [S126M, P127A, S128G]; [S126M, P127A, S128G, S160D]; and [G116V, S126N, P127S, S128A, S160D].

To illustrate the significance of the approach used in this invention for obtaining new proteases suited for application in laundry detergents, i.e. by using representative laundry application testing as primary selection criterion, the results of the wash performance tests of mutant PB92 proteases were compared with biochemical parameters as usually determined in protein biochemical and enzymological research. These results allow the conclusion that any relation between parameters determining affinity for defined substrates and kinetics of the proteolytic reaction and wash performance is absent (see Table 1 of Example 1).

Therefore, it is of course also possible to combine two or more mutants with different properties in one enzyme product or in the same washing process. Such combination may or may not have a synergistic effect.

The invention comprises also the use of one or more mutant proteolytic enzymes, as defined hereinbefore, in a detergent composition or in a washing process.

Finally, it will be clear that by deletions or insertions of the amino acids in the protease polypeptide chain, either created artificially by mutagenesis or naturally occurring in proteases homologous to PB92 protease, the numbering of the amino acids may change. However, it is to be understood that positions homologous to amino acid positions of PB92 protease will fall under the scope of the claims.

The following Examples are offered by way of illustration and not by way of limitation.

EXPERIMENTAL SECTION

Materials and methods

Construction of PB92 protease mutants

The basic construct from which the mutagenesis work started, is referred to as pM58 in detail described in EP-A-0283075.

The strategy followed comprised three phases:
a. Construction of mutagenesis vector M13M1
b. Mutation procedure
c. Construction of pM58δEco and subcloning of the mutated DNA fragment in this vector.

1.a. Construction of mutagenesis vector M13M1

The basic construct pM58 was digested with restriction enzymes HpaI and BalI. The 1400 bp fragment containing the PB92 protease gene was purified on low melting agarose (Maniatis, Molecular Cloning, A Laboratory Manual, Cold Spring Harbor, 1982 ). Vector M13MP11 (Messing et al., Nucl. Acid. Res. 9, (1981) 303-321) was digested with SmaI. The 1400 bp DNA fragment in question was ligated into this vector and transfected to E. coli JM101 according to the procedures described by Cohen et al., Proc. Natl. Acad. Sci. USA 69, (1972) 2110-2114.

After phage propagation in E. coli JM101, ssDNA was isolated (Heidecker et al., Gene 10, (1980) 69-73), and the insert and its orientation were checked by DNA sequencing using the method described by Sanger, Proc. Natl. Acad. Sci. USA 74 (1977)6463.

The vector suitable for mutagenesis was obtained and named M13M1. The procedure described above is schematically depicted in FIG. 1A.

1.b. Mutation procedures

Mutagenesis was performed on M13M1 using ssDNA of this vector and dsDNA of M13mp19 (Messing et al. Nucleic Acids Res. 9, (1988) 303-321), which latter vector was digested with the restriction enzymes EcoRI and HindIII, followed by purification of the large fragment on low melting agarose.

Mutagenesis was performed as described by Kramer et al., Nucleic Acids Res. 12, (1984) 9441-9456 with the modification that E. coli JM105 instead of E. coli WK30-3 was used to select for mutants.

The length of the oligonucleotides used to create the specific mutations was 22 nucleotides. Region specific mutation used to create several mutations at the time in a specific DNA sequence, was performed using an oligonucleotide preparation with a length of 40 nucleotides with all four nucleotides randomly incorporated in the sites corresponding to the amino acid(s) to be mutated.

After mutagenesis potential mutants were checked for the relevant mutation by sequence analysis using the dideoxy method of Sanger, see above. The entire single strand gap (see FIG. 1B) was sequenced to confirm the absence of secondary mutations. The procedure is schematically shown in FIG. 1B.

The described procedure is useful for generating DNA fragments with mutations in the 3' part of the protease gene (amino acids 154-269).

It will be evident to those skilled in the art that, in order to generate DNA fragments with mutations in the 5' part of the protease gene in a Bacillus vector, alternative restriction enzymes can be used and modified PB92 proteases genes can be constructed analogous to the method of FIG. 1A.

1.c. Construction of pM58δEco and subcloning of DNA fragments containing the mutations in this vector (FIG. 1C)

To construct pM58δEco, pM58 was digested with restriction enzyme EcoRI and ligated with T4 ligase under diluted conditions. The ligation mixture was used to transform form B. subtilis 1-A40 (Bacillus Genetic Stock Centre, Ohio) according to the method of Spizizen et al., J. Bacteriol. 81 (1961) 741-746.

Cells from the transformation mixture were plated on minimal plates containing 20 μg/ml neomycin as described in Example 1 of EP-A-0283075.

Plasmid DNA of transformants was isolated according to the method described by Birnboim and Doly, Nucleic Acids Res. 7 (1979) 1513-1523 and characterized by restriction enzyme analysis. In this way pM58δEco was isolated (see FIG. 1c).

To produce mutant enzyme, the DNA fragments of M13M1 containing the desired mutations generated as described in section 1.b. were subcloned into pM58δEco. dsDNA of M13M1 (described above) was digested with EcoRI and ligated into the EcoRI site of pM58δEco. The ligation mixture was used to transform B. subtilis DB104, Doi, J. Bacteriol. (1984) 160, 442-444, using the method of Spizizen et al., see above.

Cells from the transformation mixture were plated on minimal plates containing 20 μg/ml neomycin and 0.4% casein (EP-A-0283075). DNA of protease producing transformants was isolated according to the method described by Birnboim and Doly, (see above) and characterized by restriction enzyme analysis.

2. Production of mutant proteases

Transformants of DB104 which were determined to contain the vector with the mutated protease gene, were inoculated in 10 ml Tryptone Soya Broth (TSB) containing 20 μg/ml neomycin and incubated for 24 hours at 37° C. Samples of the culture (0.1 ml) were inoculated in 500 ml shake flasks containing 100 ml protease production medium: 12.5 g/l Yeast Extract (Difco), 0.97 g/l $CACl_2.6H_2O$, 2.25 g/l $MgCl_2.6H_2O$, 20 mg/l $MnSO_4.4H_2O$, 1 mg/l $COCl_2.6H_2O$, 0.5 g/l citrate, 0.5 ml/l antifoam 5693, 6% w/v maltose, 0.2M phosphate buffer pH 6.8 and 20 μg/ml neomycin.

After incubation for 65 hours under constant aeration, protease activity of the cultures was assayed using dimethylcasein as substrate using the method described by Lin et al., J. Biol. Chem. 244 (1969) 789-793. To produce larger representative amounts of wild-type PB92 and mutant PB92 proteases, these strains were also grown at 37° C. in aerated fermentors of 10 l volume or more, using essentially the same production medium as used for the shake flasks.

The broths obtained were used for protease purification.

3. Purification and concentration of wild-type PB92 protease and its mutants The mutant and wild-type PB92 protease produced by Bacillus subtilis DB104 in shake flasks or 10 l fermentors were purified by cation exchange chromatography using Zeta-Prep ® disks or cartridges (PS-type, LKB). Fermentation broth was centrifuged (3000xg, 10 min) and the supernatant diluted 10-fold with 10 mM sodium phosphate buffer pH 5.5 and subsequently loaded onto the cation exchanger. After washing with several cartridge volumes phosphate buffer, the protease was eluted by including 0.4M NaCl into the phosphate buffer. Fractions containing protease activity were pooled and concentrated by ultrafiltration using an Amicon stirred cell, equipped with a PM-10 filter. The NaCl concentration was reduced to approximately 50mM by diluting and concentrating the protease solution with phosphate buffer, after which it was stored at −80° C. at a protein concentration of between 1-10 mg/ml.

Alternatively, for the recovery of the PB92-protease mutants from the broths of larger scale fermentations, CaCl$_2$ (1% w/w) and acetone (30% w/w) were added. After filtration to remove the cell mass, the protease was precipitated from the obtained filtrate, by addition of 0.2-2% (w/w) of CaSO$_4$.2H$_2$O and by further addition of acetone to a final concentration of >60% w/w. The precipitate was separated by filtration and sparged with acetone followed by drying, to give a crude enzyme powder (CEP).

4. Analytical techniques to check the purity purified proteases

Proteases were considered pure when a single band or peak was found by electrophoresis and high performance gel electrophoresis (HPLC), respectively.

Polyacrylamide gel-electrophoresis (PAGE) in the presence of sodium dodecyl sulphate (SDS) was carried out according to Laemmli, Nature, 227 (1970) 680–685. Denaturation of the protein samples by SDS at 100° C., however, must be preceded by inactivation of the protease activity in order to prevent autodegradation. This can be done by incubation with phenylmethylsulfonyl fluoride (PMSF) (1 mM, 30 min, room temperature) or precipitation with trichloroacetic acid (TCA, 8%, 30 min, on ice). Native PAGE was carried out at pH 7.45 (gel buffer consisting of 20 mM histidine (His) and 50 mM 3-[N-morpholino]propanesulfonic acid (MOPS) in 5% polyacrylamide gels (ratio of acrylamide:bisacrylamide 20:1). Protein samples were loaded on top of slab gels and electrophoresed towards the cathode. The same His/MOPS buffer was used as electrophoresis (tank) buffer, but at pH 6.3. After electrophoresis (1½-2 h at 350 V), the gel was soaked in 8% acetic acid to fix the proteins in the gel and subsequently stained with Coomassie Brilliant Blue R250 and destained according to standard procedures.

The purity check by HPLC. made use of a cation exchange column (MonoS-Pharmacia Fine Chemicals) and a gel filtration column (TSK 2000 SW-LKB). The former was run in a 10 mM sodium phosphate buffer pH 5.5 and elution of the bound protease was obtained using a linear gradient of 10-300 mM sodium phosphate pH 5.5. The gel filtration column was run in 0.25M sodium acetate pH 5.5.

5. Determination of the protease concentration

For the determination of the protein concentration in a purified protease solution, use was made of
 i) extinction measurements at 280 nm using the calculated extinction coefficient ($\epsilon_M$), and
 ii) active site titration.

The extinction coefficient at 280 nm was calculated from the number of tryptophans ($\epsilon_M=5,600$ M$^{-1}$.cm$^{-1}$) and tyrosines ($\epsilon_M=1,330$ M$^{-1}$.cm$^{-1}$) per enzyme molecule. For PB92 protease the $\epsilon_M$ was 26,100 M$^{-1}$.cm$^{-1}$ (3 Trp, 7 Tyr residues) equivalent to $$E_{1\,cm}^{1\%}$$

the measured at 280 nm=9.7 (M$_r$=26,729 Da), was used. In case of mutants with an altered number of Trp's and Tyr's, corrections were made accordingly.

An estimation of the number of active enzyme molecules was obtained with an active site titration. Since the widely used method with N-transcinnamoylimidazole (M. L. Bender et al., J. Am. Chem. Soc. 88, (1966) 5890–5931) proved not to work satisfactorily for PB92 protease, we developed a method using PMSF instead. Hereto, a protease solution with an estimated enzyme concentration (from the 280 nm absorption) was mixed with 0.25, 0.50, 0.75, 1.00 and 1.25 equivalents of PMSF, respectively, and allowed to react for one hour at room temperature in 10 mM sodium phosphate pH 6.5. The enzyme concentration has to be at least 50 $\mu$M.

Residual activity was measured spectrophotometrically using succinyl-L-alanyl-L-alanyl-L-prolyl-L-phenyl-alanyl-paranitroanilide (sAAPFpNA) as a substrate (see below). The purity (and hence concentration) of PMSF was determined by NMR-spectroscopy and stock solutions were made in isopropanol. The results from the active site titration were found to be in agreement with the results from the purity check with HPLC.

6. Determination of kinetic parameters of wild type and mutant proteases

1°. Activity on protein substrates (casein) was measured at pH 10.0 as described in British Patent Specification 1,353,317 (expressed in ADU's=Alkaline Delft Units).

2°. The turnover number with casein as substrate was measured in a pH-stat. The reaction chamber of the pH-stat (Radiometer, Copenhagen) contained 10 ml 0.1M KCl with 50 mg casein (Hammerstein, Merck). Protons, liberated upon hydrolysis of casein by PB92 protease were titrated with 10 mM NaOH while the pH was maintained at 10.0 (at 40° C. and under a flow of nitrogen gas).

3°. Activity on synthetic peptides was measured using sAAPFpNA. The (yellow) paranitronanilide (pNA) formed was measured spectrophotometrically at 410 nm: $\epsilon_M=8,480$ M$^{-1}$.cm$^{-1}$, (E. G. Delmar et al., Anal. Biochem. 94 (1979) 316-320) with a UVIKON 860 (KONTRON) spectrophotometer equipped with a thermostat controlled six-position cell changer. The kinetic parameters $k_{cat}$ and $K_m$ were obtained from initial rate measurements at various substrate concentrations (for PB92 protease from 0.1–6.0 mH) and fitting the data to a hyperbolic function by non-linear regression using the multivariate secant iterative method. The specificity constant $k_{cat}/K_m$ was calculated. Measurements were carried out at 25° C. in a final volume of 1 ml containing 0.1M TRIS-HCl+0.1M NaCl pH 8.6. The sodium chloride was necessary since in its absence PB92 protease showed non-linear Lineweaver-Burk plots, what could have been caused by substrate inhibition. The substrate was first dissolved in DMSO to a concentration of 200 mM and subsequently diluted with 0.1M TRIS-HCl pH 8.6 to give a stock solution of 20 mM (determined spectrophotometrically at 315 $\epsilon_M=14,000$ M$^{-1}$.cm$^{-1}$). No corrections were made for the varying concentrations of DMSO (0.05–3.0 % v/v).

7. Oxidation of PB92 proteases

The sensitivity of the PB92 proteases for oxidation by H$_2$O$_2$ was tested according to the method described by Estell et al., J. Biol. Chem. 260 (1985) 6518–6521, except that:
 i) 20 mM H$_2$O$_2$ was used instead of 100 mM, and
 ii) 20 mM sodium perborate combined with 10 mM TAED was used as an additional oxidant.

8. Wash performance test

PB92 protease mutants were tested in a specially developed washing test, using cotton and polyester/cotton swatches, soiled with milk, blood and ink (5.0×5.0 cm, obtained from EMPA, St. Gallen, Switzerland and designated with the numbers 116 and 117).

The washing tests were performed in an Atlas Launderometer LEF-FC, equipped with stainless steel test vessels each containing a defined detergent composition plus the protease to be tested (PB92 protease mutants or PB92 protease). Unless stated otherwise the tests were carried out for 30 minutes at a desired temperature. After washing, the swatches were air-dried and the reflectance of the test cloths was measured at 680 nm with a Photovolt photometer (Model 577) equipped with a green filter. Reflectance data measured on the test swatches washed with detergents containing the respective PB92 protease mutants were compared with reflectance data from a comparable series of measurements with detergents containing PB92 protease. Wash performance values of the mutant proteases were calculated by dividing the amount of protein of PB92 protease (mg) by the amount of protein of mutant protease (mg) which was needed to achieve the same reflectance, ×100%.

water of 15° GH, were each loaded with two cotton and two polyester/cotton swatches. The composition of the powder detergent IEC was as follows:

| Component | wt % |
|---|---|
| Linear sodium alkyl benzene sulphonate (mean chain length of alkane chain C11.5) | 6.4 |
| Ethoxylated tallow alcohol (14 EO) | 2.3 |
| Sodium soap | 2.8 |
| Sodium tripolyphosphate (STPP) | 35.0 |
| Sodium silicate | 6.0 |
| Magnesium silicate | 1.5 |
| Carboxy methyl cellulose | 1.0 |
| Sodium sulphate | 16.8 |
| Sodium perborate tetrahydrate | 18.5 |
| TAED | 1.5 |
| Miscellaneous + water | up to 100 |

To each vessel a selected purified PB92 protease mutant was added in a concentration varying between 0 and 1.74 mg (purified) protease per liter sud. One vessel was used for testing PB92 protease in the same way, for comparison. The washing tests were carried out at 40° C. The results are shown in Table 1.

TABLE 1

Properties of PB92 protease and some of its mutants

| Protease | Wash performance relative to PB92 protease[#] (%) Detergent concentration in the sud | | Specific activity relative to PB92 protease* (%) | Kinetic parameters[+] | | |
|---|---|---|---|---|---|---|
| | 4 g/l | 7 g/l | | $k_m$ (mM) | $k_{cat}$ (1/s) | $k_{cat}/K_m$ (1/s · mM) |
| PB92 protease | 100 | 100 | 100 | 1.0 | 105 | 102 |
| M216-oxidized | 80 | 80 | 50 | 1.1 | 10 | 9 |
| M216S | 100 | 90 | 40 | 1.3 | 7 | 5 |
| M216Q | 110 | 90 | 37 | 1.7 | 5 | 3 |
| M216C | 50 | | 36 | 1.2 | 37 | 30 |
| S160K | 21 | 25 | 47 | 1.2 | 12 | 11 |
| S160D | 215 | 155 | 73 | 1.2 | 14 | 12 |
| S160C | 108 | | 48 | 0.98 | 20 | 21 |
| N212D | 220 | 75 | 100 | 1.2 | 104 | 86 |
| S160G, N212D | 170 | | 76 | 1.7 | 30 | 18 |
| N212S | 78 | | 85 | | | |
| E134K | 13 | | 95 | 1.1 | 56 | 49 |
| A166D, M169I | 136 | | 100 | | | |
| S160D, M216Q | 70 | 35 | 12 | | | |
| S160D, M216S | 145 | 70 | 17 | | | |
| M117L, M216Q | 68 | 70 | 27 | 0.9 | 4 | 2 |
| M117L, M216S | 61 | 80 | 36 | 1.7 | 8 | 8 |
| G116V, S126V, P127E, S128K | 250 | 105 | 43 | 3.0 | 260 | 86 |
| G116V, S126L, P127N, S128V | 165 | 165 | 81 | 4.1 | 260 | 65 |
| G116V, S126L, P127Q, S128A | 200 | 200 | 62 | 5.1 | 290 | 57 |
| G116V, S126V, P127M | 250 | 250 | 69 | 2.1 | 207 | 98 |
| S126M, P127A, S128G | 200 | 200 | 115 | 2.0 | 356 | 180 |
| M169I, M216S | 80 | 95 | 44 | | | |
| G116V, S126Y, P127G, S128L | 80 | 75 | 69 | | | |
| G116V, S126N, P127H, S128I | 90 | 110 | 115 | | | |
| G116V, S126H, P127Y | 113 | 87 | 73 | | | |
| G116V, S126R, P127S, S128P | 130 | 175 | 81 | | | |
| G116V, S126F, P127Q | 225 | 95 | | | | |
| G116V, S126G, P127Q, S128I | 75 | 110 | 95 | 3.2 | 41 | 13 |
| G116V, S126F, P127L, S128T | 150 | 80 | 19 | 11.0 | 200 | 19 |

[#]Wash performance was measured in STPP containing powder detergent IEC at 40° C.
*PB92 protease has 100% specific activity by definition. Activity determined by the ADU method.
[+]Assay conditions: substrate s-A-A-P-F-pNA; buffer 0.1M TrisHCl, pH 8.6; 0.1M NaCl; 25° C.

EXAMPLE 1

A. The wash performance of various PB92 protease mutants in European powder detergents was determined according to the method described above.

Stainless steel test vessels, each containing a stated amount of powder detergent IEC, dissolved in 250 ml B. The wash performance test was repeated at 25° C. with the same detergent containing some of the PB92 protease mutants. PB92 protease was again used as a reference. Other test conditions were the same as described above. The results are shown in Table 2.

TABLE 2

Wash performance of PB92 protease mutants at 25° C. in STPP containing powder detergent, relative to PB92 protease (%).

| Protease | Wash performance (%) Detergent concentration in the sud | |
|---|---|---|
| | 4 g/l | 7 g/l |
| M216S | 90 | 80 |
| M216Q | 95 | 80 |
| N212D | 250 | 135 |
| S160D | 185 | 120 |

C. The wash performance of the proteases was also determined in a non-phosphate bleach containing European powder detergent, in a Launderometer at 25° C. and 40° C. PB92 protease was again used as a reference. Other test conditions were the same as described above. The results are shown in Table 3.

TABLE 3

Wash performance of PB92 protease mutants at 25° C. and 40° C. in a non-phospate bleach containing European powder detergent, relative to PB92 protease (%).

| Protease | Wash performance (%) Detergent concentration in the sud | | | |
|---|---|---|---|---|
| | 4 g/l temperature 25° C. | 7 g/l temperature 25° C. | 4 g/l temperature 40° C. | 7 g/l temperature 40° C. |
| M216S | 80 | 85 | 100 | 90 |
| M216Q | 80 | 80 | 120 | 100 |
| N212D | 170 | 105 | 200 | 75 |
| S160D | 170 | 105 | 230 | 165 |

EXAMPLE 2

PB92 protease mutant M216S was tested on storage stability in the powder detergent IEC. described in Example 1. Storage stability was investigated in climate boards at 30° C. and 80% relative humidity (RH). The protease for this experiment was encapsulated as follows:

A mixture was made containing (in w/w): 2% purified protease, 50% nonionic (ethoxylated $C_{14}$-$C_{18}$ alcohol with 50-80 E.O. units), 5% $TiO_2$, 3-10% $CaSO_4.2H_2O$, and $Na_2SO_4$ ad 100%. The mixture was heated to 65°-90° C. and cooled to room temperature. The obtained solidified mixture was ground into particles. Particles of 0.5 to 1 mm in diameter were sieved out and used for storage tests in detergents.

3.5 g of the powder detergent IEC, containing mutant M216S at a concentration of 6140 ADU/g detergent was stored in 18 ml vials. For comparison PB92 protease was stored under the same conditions. After 2, 4, 5 and 6 weeks the residual activity of the proteases was measured. The results are shown in Table 4.

TABLE 4

Residual activity of PB92 protease and its mutant M216S after storage (in weeks) at 30° C. and 80% RH in powder detergent.

| Protease | Residual activity (%) | | | | |
|---|---|---|---|---|---|
| | 0 w | 2 w | 4 w | 5 w | 6 w |
| PB92 protease | 100 | 25 | 5 | 3 | 2 |
| M216S | 100 | 68 | 31 | 20 | 11 |

EXAMPLE 3

PB92 protease and various PB92 protease mutants were tested on storage stability in a powder detergent. In the storage stability test the proteases were used in an encapsulated form.

The protease products were made by mixing the following components at 80° C.:

| Component | wt % |
|---|---|
| AE* | 50 |
| $TiO_2$ | 2 |
| protease (CEP) | 7 |
| PVP** | 1.5 |
| BHT*** | 1 |
| $Na_2SO_4$ | balance |

*AE = $C_{14}$-$C_{18}$ alcohol polyethoxylate. The alcohol was ethoxylated with 50-80 ethylene oxide (EO) groups.
**PVP = polyvinyl pyrrolidone K17
***BHT = 2,6-bis(t-butyl)-4-methylphenol.

This mixture was encapsulated by prilling, essentially as described in British Patent Specification No. 1,603,640. The particle fraction with a particle size between 0.3 and 0.8 mm was used to determine the storage stability of the proteases. The encapsulated protease (140 mg) was mixed with ALL ® base (6.4 g) and sodium perborate tetrahydrate (0.6 g). [ALL is a registered trade mark of Unilever Nev.]. The ALL base powder used did not contain enzymes or bleaching agents.

The enzyme/detergent/sodium perborate tetrahydrate mixture was incubated at 30° C. and 80% RH. In Table 5 the residual activity after storage for the indicated period of time is given.

TABLE 5

Residual activity of PB92 protease and some of its mutants after storage (in weeks) at 30° C. and 80% RH in a bleach containing powder detergent.

| Protease | Residual activity (%) | | | |
|---|---|---|---|---|
| | 0 w | 1 w | 3 w | 5 w |
| PB92 protease | 100 | 51 | 25 | 15 |
| M216Q | 100 | 94 | 84 | 52 |
| M216S | 100 | 89 | 83 | 50 |
| S160D | 100 | 47 | 20 | 9 |
| N212D | 100 | 59 | 31 | 19 |

EXAMPLE 4

PB92 protease and various PB92 protease mutants were encapsulated following the method described in Example 3. In this Example, however, 70 mg of encapsulated protease with a particle size between 0.3 and 0.9 mm were mixed with 3.2 g of ALL and 0.3 g of sodium perborate tetrahydrate. The samples were stored at 30° C. in 18 ml vials in a vacuum dessicator. Vacuum was applied (25 mm Hg) during the first three days of the storage period.

By applying a vacuum the rate of water vapor transport was increased, so the system reached its equilibrium at 80% RH faster than in systems that do not apply a vacuum. The RH of 80% was established by a saturated solution of potassium bromide.

In Table 6 residual activities after the indicated period of storage (in weeks) are given.

TABLE 6

Residual activity of PB92 protease and some of its mutants after storage at 30° C. and 80% RH in a bleach containing detergent.

| Protease | Residual activity (%) | | | |
|---|---|---|---|---|
| | 0 w | 1 w | 2 w | 3 w |
| PB92 protease | 100 | 27 | 22 | 14 |
| M216Q | 100 | 63 | 53 | 44 |
| M216S | 100 | 55 | 49 | 31 |

TABLE 6-continued

Residual activity of PB92 protease and some of its mutants after storage at 30° C. and 80% RH in a bleach containing detergent.

| Protease | Residual activity (%) | | | |
|---|---|---|---|---|
| | 0 w | 1 w | 2 w | 3 w |
| S160D | 100 | 23 | 18 | 13 |

EXAMPLE 5

The following liquid detergent composition was prepared:

| Component | Wt % |
|---|---|
| C$_{10}$–C$_{13}$ linear alkylbenzene-sulfonic acid | 12 |
| C$_{13}$ alcohol polyethoxylate, 8 EO | 13 |
| lauric acid | 8 |
| oleic acid | 4 |
| triethanolamine | 6 |
| 1,2 propanediol | 6 |
| ethanol | 5 |
| sodium citrate | 4 |
| diethylenetriamine-pentaacetic acid | 0.3 |
| calcium formate | 0.12 |
| sodium formate | 1 |
| borax | 1.9 |
| NaOH, 25% w/w solution | to pH 11.2 |
| water | balance |

PB92 protease and various PB92 protease mutants were added to this composition in an amount to provide an initial protease concentration of 0.13% w/w.

Protease stability (in % of residual activity) was determined after storage of the protease containing composition at 37° C. for the indicated number of days. The results are shown in Table 7.

TABLE 7

Residual activity of PB92 protease and some of its mutants after storage at 37° C. in a liquid detergent composition.

| Protease | Residual activity (%) | | | | |
|---|---|---|---|---|---|
| | 0 d | 5 d | 11 d | 15 d | 21 d |
| PB92 protease | 100 | 23 | 10 | 5 | 3 |
| S160D | 100 | 57 | 30 | 14 | 8 |
| M216Q | 100 | 59 | 32 | 18 | 9 |
| M216S | 100 | 45 | 18 | 10 | 5 |
| N212D | 100 | 38 | 14 | 9 | 4 |

EXAMPLE 6

PB92 protease and some of its mutants were formulated as follows. With each protease a mixture was made consisting of the following components:

| Component | Wt % |
|---|---|
| Amylogum CLS | 45 |
| sucrose | 23 |
| sorbitol | 17 |
| glycerol | 4 |
| paraffin oil | 3 |
| NaH$_2$PO$_4$ | 0.5 |
| protease (CEP) | 5.0 |
| PVP K17 | 1.5 |
| TiO$_2$ | 1 |

From these mixtures granulates were produced, essentially following the procedure described in Example 5 of U.S. Pat. No. 4,242,219, except that: 1° the mixture described in said example is replaced by the above mixture; 2° orifices were used with a diameter of 0.7 mm instead of 1.0 mm; 3° the granules were not coated.

These granules (140 mg) were mixed with ALL base (6.4 g) and sodium perborate tetrahydrate (0.6 g) and placed in 36 ml vials.

Protease stability (in % of residual activity) was then determined after storage of the vials at 30° C. and 80% RH for the indicated number of weeks. The results are shown in Table 8.

TABLE 8

Residual activity of granulates of PB92 protease and some of its mutants after storage at 30° C. and 80% RH in detergent.

| Protease | Residual activity (%) | | | |
|---|---|---|---|---|
| | 0 w | 1 w | 3 w | 5 W |
| PB92 protease | 100 | 45 | 29 | 17 |
| M216Q | 100 | 93 | 66 | 45 |
| M216S | 100 | 90 | 70 | 41 |

EXAMPLE 7

Prilled products of PB92 protease and some of its mutants were produced and mixed with detergent and bleach as described in Example 3.

The storage stability of these samples (in % of residual activity) was determined at 30° C. and 60/80% RH (alternatingly 60% RH for 12 hours and 80% RH for 12 hours). The results are shown in Table 9.

TABLE 9

Residual activity of prilled products of PB92 protease and some of its mutants after storage at 30° C. and 60/80% RH.

| Protease | Residual activity (%) | | | |
|---|---|---|---|---|
| | 0 w | 1 w | 3 w | 5 w |
| PB92 protease | 100 | 70 | 34 | 15 |
| M216Q | 100 | 98 | 88 | 67 |
| M216S | 100 | 93 | 87 | 48 |
| S160D | 100 | 67 | 35 | 10 |
| N212D | 100 | 75 | 53 | 26 |

EXAMPLE 8

Granules containing PB92 protease and some of its mutants were produced and mixed with detergent and bleach as described in Example 6.

The storage stability of these samples (in % of residual activity) was determined after incubation for the indicated period of time at 30° C. and a RH which was kept at 50% for 12 hours and at 80% for 12 hours, alternatingly. The results are shown in Table 10.

TABLE 10

Residual activity of granulates of PB92 and some of its mutants after storage at 30° C. and 60/80% RH.

| Protease | Residual activity (%) | | | |
|---|---|---|---|---|
| | 0 w | 1 w | 3 w | 5 w |
| PB92 protease | 100 | 54 | 39 | 28 |
| M216Q | 100 | 93 | 81 | 67 |
| M216S | 100 | 99 | 87 | 72 |

EXAMPLE 9

PB92 protease and some of its mutants were tested on storage stability in a bleach containing powder detergent at 30° C. and 80% RH. For this experiment the proteases were used in an encapsulated form. Each protease was encapsulated as follows:

At 80° C. a mixture was made consisting of the following composition:

| Component | wt % |
|---|---|
| Nonionic * | 45 |
| TiO$_2$ | 2 |
| protease (CEP) | 10 |
| Na$_2$SO$_4$ | balance |

* Nonionic = C$_{14}$-C$_{18}$ alcohol polyethoxylate (50–80 EO groups)

The above mixture was allowed to cool to room temperature. The solidified mixture was ground into smaller particles. Particles of 0.3 to 0.8 mm were sieved out and used for the storage experiment.

For the storage experiment 140 mg of each encapsulated protease was mixed with 6.4 g of ALL base powder detergent and 0.6 g of sodium perborate tetrahydrate. The ALL base powder contained neither enzymes nor sodium perborate. The ALL base/protease/sodium perborate tetrahydrate mixtures were incubated at 30° C. and 80% RH.

After storage for 0, 1, 2 or 4 weeks the protease stability, in terms of % residual activity, was determined for each protease. The results are shown in Table 11.

TABLE 11

Residual activity of PB92 protease and some of its mutants after storage at 30° C. and 80% RH in a bleach containing powder detergent.

| Protease | Residual activity (%) | | | |
|---|---|---|---|---|
| | 0 w | 1 w | 2 w | 4 w |
| PB92 protease | 100 | 61 | 36 | 12 |
| [S160D, M216Q] | 100 | 78 | 58 | 35 |
| [S160D, M216S] | 100 | 86 | 68 | 39 |

EXAMPLE 10

PB92 protease mutants were tested in a washing test under essentially the same conditions as described in Example 1, except that 0.375 g liquid detergent of the following composition was added to 250 ml water of 5° GH in the Launderometer vessel.

| Component | wt % |
|---|---|
| lauric acid | 8 |
| oleic acid | 4 |
| C$_{10}$-C$_{13}$ linear alkylbenzene sulphonic acid | 12 |
| C$_{13}$ alcohol polyethoxylate, 8 EO | 13 |
| triethanolamine | 6 |
| 1.2 propanediol | 6 |
| ethanol | 5 |
| sodium hydroxide, 45% w/w | 4 |
| sodium citrate | 4 |
| water | up to 100 |
| (pH of the sud 7.2) | |

The wash performance of the various proteases in this liquid detergent was determined in a Launderometer at 25° C. for 30 minutes. After washing the reflectance of the test clothes were measured as described in Example 1. Wash performance of the mutant proteases was determined as described in Example 1. The results are shown in Table 12.

TABLE 12

Wash performance of PB92 protease mutants at 25° C. in a liquid detergent.

| Protease | Wash performance | Specific activity relative to PB92 protease (%) |
|---|---|---|
| 212D | + | 100 |
| 160D | + | 73 |

TABLE 12-continued

Wash performance of PB92 protease mutants at 25° C. in a liquid detergent.

| Protease | Wash performance | Specific activity relative to PB92 protease (%) |
|---|---|---|
| S160G, N212D | + | 76 |
| M216S | 0 | 40 |
| M216Q | 0 | 37 |

0: 100% ± 20% wash performance relative to PB92 protease (retained wash performance).
+: >120% wash performance relative to PB92 protease.
−: <80% wash performance relative to PB92 protease.

The wash performance of the various proteases was determined in the commercially available liquid detergents Tide ®, Wisk ® and Ariel ®. The stainless steel vessels contained either 0.375 g Tide in 250 ml water of 5° GH, 0.375 g Wisk in 250 ml water of 5° GH or 1.25 Ariel in 250 ml water of 15° GH, respectively. Wash performance was determined at 25° C. or 40° C. Other conditions were the same as described in Example 1. The results are shown in Table 13.

TABLE 13

Wash performance of PB92 protease mutants in Tide, Wisk and Ariel at 25° C. and 40° C.

| Protease | Tide | | Wisk | | Ariel |
|---|---|---|---|---|---|
| | 25° C. | 40° C. | 25° C. | 40° C. | 40° C. |
| N212D | + | + | + | + | 0 |
| S160D | + | + | + | + | + |
| M216Q | 0 | + | 0 | + | + |
| M216S | ND | 0 | 0 | 0 | 0 |
| S160Q | − | − | − | − | − |
| S160N | − | − | − | − | 0 |
| S160K | − | − | − | − | − |
| S160A | − | − | − | − | − |
| S160D, M216Q | + | + | + | + | + |
| S160D, M216S | 0 | − | + | + | 0 |
| M117L, M216Q | ND | − | ND | − | 0 |
| M117L, M216S | ND | − | ND | − | − |

ND = not determined
0: 100 ± 20% wash performance relative to PB92 protease.
+: >120% wash performance relative to PB92 protease.
−: <80% wash performance relative to PB92 protease.

EXAMPLE 11

The wash performance of PB92 protease mutants was determined in a statistical real scale washing machine test by TNO, Delft, the Netherlands (Cleaning Techniques Research Institute). The wash performance of these mutants was compared with PB92 protease.

All proteases were dosed in IEC detergent on the basis of protein weight (0.007% w/w). Based on activity these dosages yielded:

| PB92 protease | 1460 ADU/g detergent |
|---|---|
| M216S | 679 ADU/g detergent |
| M116Q | 479 ADU/g detergent |
| S160D | 1080 ADU/g detergent |
| N212D | 1455 ADU/g detergent |

With each detergent protease composition 8 washing tests were carried out at 40° C. in identical AEG Turnamat twinup washing machines. In each washing machine 170 g detergent was used. During the tests, the investigated detergents were used in such a way that each powder underwent the same number of washing cycles in each machine.

During the tests normal tap water as supplied in the city of Delft with the following mean specifications was used:

| | |
|---|---|
| alkalinity (M): | 2.2 mmol/l |
| hardness (H): | 1.6 mmol/l (9°GH) |
| temperature: | 20° C. |

Soil and stain removal from test clothes

In each test run 6 swatches of three types of EMPA soilings on cotton (nos. 111, 116 and 117), were washed together with the soiled laundry.

The soil and stain removal of the artificially soiled test cloth was then assessed by sending tristimulus blue light perpendicular to the test cloth. The amount of light, re-emitted from the test cloth at an angle of 45°, was measured. According to IEC. publication 456, the remission value of magnesium oxide was set at one hundred. The higher the remission value, the better the washing process for a particular kind of soiling.

Load of the washing machine

The washing machines were filled with a load of 4.75 kg consisting of test clothes and laundry that became dirty in normal household use. The laundry consisted of:

6 pieces of kitchen towels
4 pieces of underwear
4 bedsheets
4 pillow cases.

If necessary, clean bedsheets and pillow cases were added to reach the required amount of load.

For each washing process the laundry was carefully selected. Each piece of cloth that was selected for in one of the machines had an equally dirty counterpart which was washed in one of the other washing machines. In this way, the soil load in each process was equal.

| Parameters of the washing process | |
|---|---|
| program | 40° C. |
| water in main wash | 19 l |
| time to highest temperature | 15 min |
| highest teperature | 43° C. |
| washing time | 45 min |
| water intake | 7 l |
| temprature after sud dilution | 30° C. |
| drain | 17 l |

5 rinses with approx. 17 liters of cold water each

The mean values of the remission (V) and the ratio (R) were determined after 8 washing tests. The results of two independant experiments are shown in the Tables 14A and 14B.

TABLE 14A

| | Removal of artificial soilings | | | | | | | |
|---|---|---|---|---|---|---|---|---|
| | EMPA swatch no. | | | | | | | |
| | 111 | | 116 | | 117 | | Total | |
| Protease | V | R | V | R | V | R | V | R |
| PB92 protease | 49 | 1.00 | 44 | 1.00 | 56 | 1.00 | 149 | 1.00 |
| M216S | 49 | 1.00 | 46 | 1.05 | 58 | 1.04 | 153 | 1.03 |

TABLE 14B

| | Removal of artificial soilings | | | | | | | |
|---|---|---|---|---|---|---|---|---|
| | EMPA swatch no. | | | | | | | |
| | 111 | | 116 | | 117 | | Total | |
| Protease | V | R | V | R | V | R | V | R |
| PB92 protease | 41 | 1.00 | 35 | 1.00 | 46 | 1.00 | 123 | 1.00 |
| M216S | 40 | 0.96 | 33 | 0.94 | 42 | 0.91 | 115 | 0.93 |
| M216Q | 42 | 1.01 | 35 | 0.99 | 43 | 0.94 | 120 | 0.98 |

In Table 15 the ratios (R) obtained from statistical real scale washing machine tests were divided by the corresponding ratio (R'), calculated from wash performance values relative to PB92 protease obtained from Launderometer washing test under similar conditions (10 g/l IEC, test cloths EMPA 116 and 117, washing time 30 min, temperature 40° C.).

TABLE 15

| Correlation between real scale washing machine test and Launderometer washing test. | |
|---|---|
| Protease | R/R' |
| PB92 protease | 1.00* |
| M216S | 1.18 |
| M216Q | 1.10 |
| S160D | 1.02 |
| N212D | 0.98 |

*by definition

Values of R/R' for mutant protease close to 1.0 indicate the correlation of real scale machine tests and Launderometer tests.

EXAMPLE 12

Figure 2A:
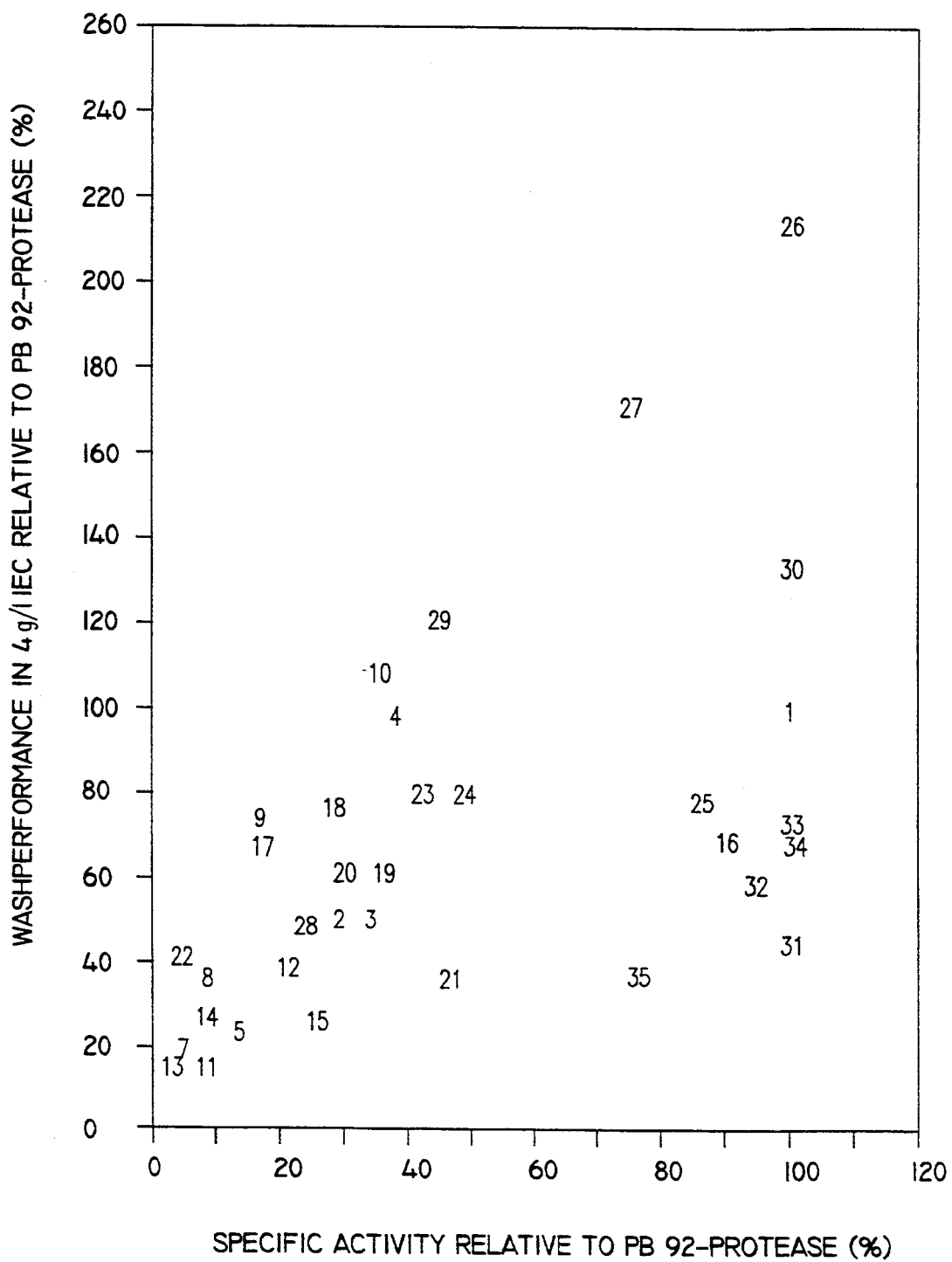
FIGS. 2A, 2B and 3 show the wash performance versus specific proteolytic activity of various PB92 protease mutants under different wash conditions.
Figure 2B:
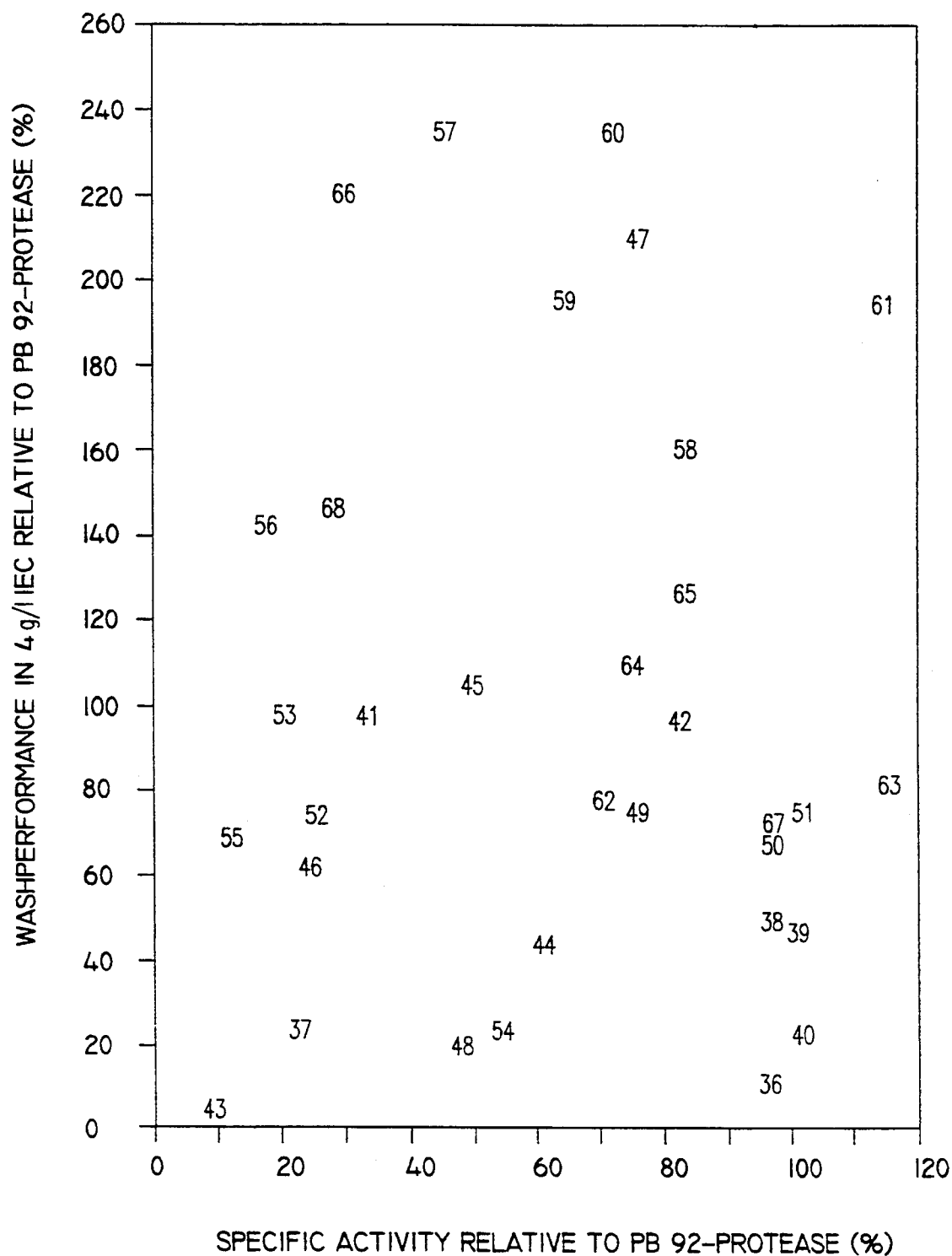

FIGS. 2A and 2B show the wash performance in 4 g IEC/l of various PB92 protease mutants according to the tests described in Example 1 relative to native PB92 protease, as a function of their specific activity. The figures in the diagram refer to the following mutant proteases:

| | | | |
|---|---|---|---|
| 1 | PB92 protease | 11 | M216 |
| 2 | M216A | 12 | M216T |
| 3 | M216C | 13 | M216W |
| 4 | M216S | 14 | M216I |
| 5 | M216L | 15 | M216G |
| 6 | M216E | 16 | M117L, H118D |
| 7 | M216K | 17 | M117L, M216Q |
| 8 | M216H | 18 | M117L, H118D, M216Q |
| 9 | M216N | 19 | M117L, M216S |
| 10 | M216Q | 20 | M117L, H118D, M216S |
| 21 | M169S | 31 | S259K |
| 22 | M216Y | 32 | W235R |
| 23 | M169I, M216S | 33 | H243R |
| 24 | M216-ox | 34 | H243R, S259K |
| 25 | N212S | 35 | D175N |
| 26 | N212D | 36 | E134K |
| 27 | S160G, N212D | 37 | W235R, S259K |
| 28 | L211Y | 38 | W235R, H243R |
| 29 | L211Y, N212S | 39 | S259K |
| 30 | A166D, M169I | 40 | T207K |
| 41 | S160N | 51 | S160I |
| 42 | S160G | 52 | S160G, M216S |
| 43 | S160P | 53 | S160G, M216Q |
| 44 | S160T | 54 | S160L |
| 45 | S160C | 55 | S160Y |
| 46 | S160Q | 56 | S160D, M216S |
| 47 | S160D | 57 | G116V, S126V, P127E, S128K |
| 48 | S160K | 58 | G116V, S126L, P127N, S128V |
| 49 | S160R | 59 | G116V, S126L, P127Q, S128A |
| 50 | S160A | 60 | G116V, S126V, P127M |
| 61 | S126M, P127A, S128G | | |
| 62 | G116V, S126Y, P127G, S128L | | |
| 63 | G116V, S126N, P127H, S128I | | |
| 64 | G116V, S126H, P127Y | | |

| | |
|---|---|
| 65 | G116V, S126R, P127S, S128P |
| 66 | G116V, S126F, P127Q |
| 67 | G116V, S126G, P127Q, S128I |
| 68 | G116V, S126F, P127L, S128T |
| 69 | G116V, S126Q, P127D |

Figure 3:
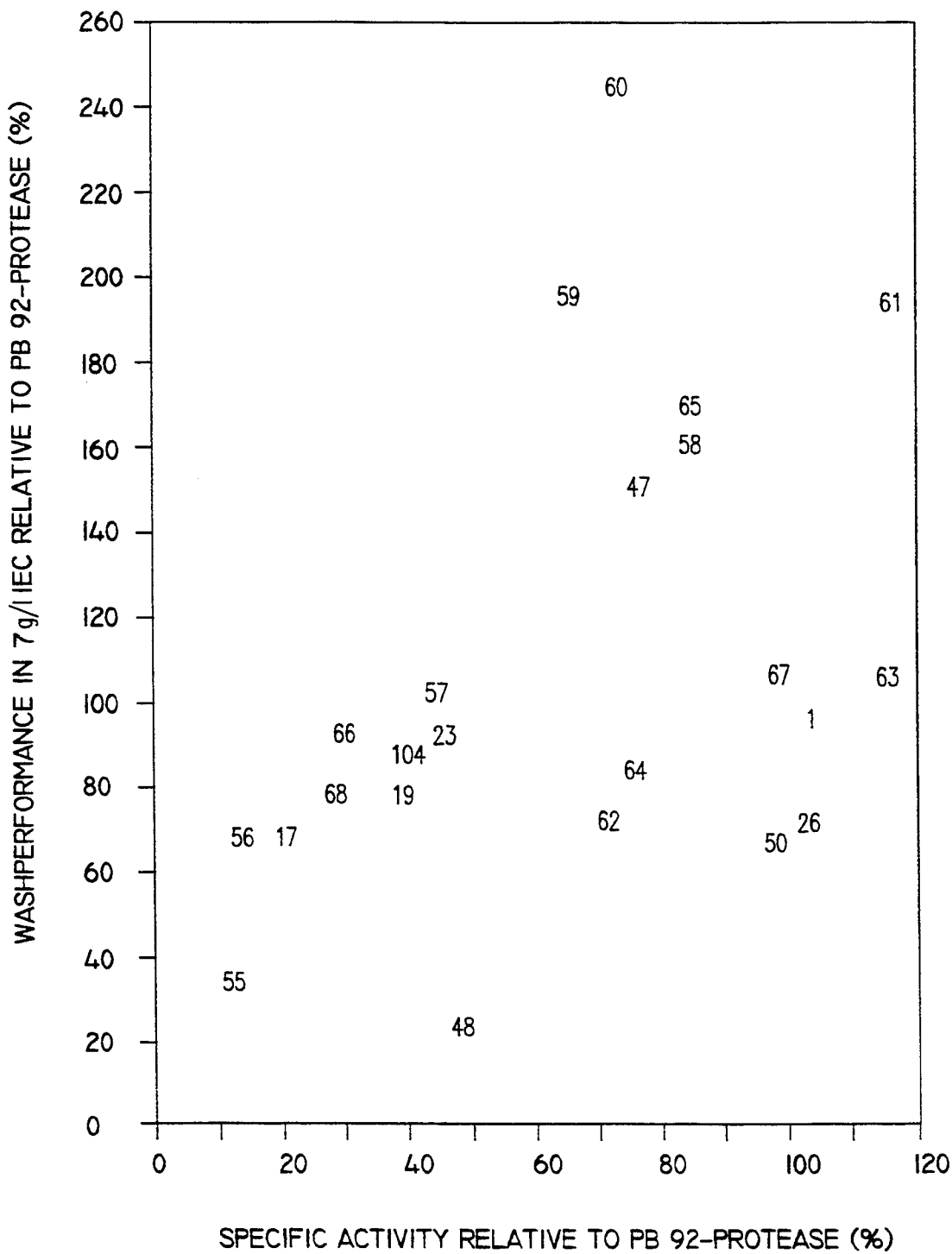

FIG. 3 shows the wash performance in 7 g IEC/l of various PB92 protease mutants according to the tests described in Example 1 relative to native PB92 protease, as a function of their specific activity. The figures in the diagram refer to the same mutant proteases as in figures as in FIGS. 2A and 2B.

All publications (including patent applications) mentioned in this specification are indicative to the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be apparent to one of ordinary skill in the art that many changes and modifications can be made thereto without departing from the spirit or scope of the appended claims.

We claim:

1. A substantially pure serine protease mutein comprising:
a substitution of an amino acid residue at a selected site corresponding to a residue position selected from the group consisting of 116, 126, 127, 128, 160, and 216 of mature PB92 protease obtained from Bacillus novo species PB92, wherein said mature PB92 protease has an amino acid sequence as shown in FIG. 4; and wherein
relative to said mature PB92 protease prior to said substitution, the mutein has demonstrated (a) improved wash performance or (b) retained wash performance and improved stability against oxidizing agents.

2. A substantially pure serine protease mutein comprising a mutation selected from the group consisting of M216S); (M216Q); (S160D); (S160D, M216Q); (S160D, (M216S); (G116V, S126V, P127E, S128K); (G116V, S126G, P127Q, S128I); (G116V, S126L, P127N, S128V); (G116V, S126L, P127Q, S128A); (G116V, S126V, P127M); (G116V, S126H, P127Y); (G116V, S126R, P127S, S128P); (G116V, S126F, P127Q); (G116V, S126F, P127L, S128T); and (S126M, P127A, S128G) of mature PB92 protease obtained from Bacillus novo species PB92, wherein said mature PB92 protease has an amino acid sequence as shown in FIG. 4 and wherein relative to said mature PB92 protease prior to said substitution, the mutein has demonstrated (a) improved wash performance or (b) retained wash performance and improved stability against oxidizing agents.

3. A substantially pure serine protease mutein comprising one set of mutations selected from the group consisting of:
 (a) G at position 116 to V;
 (b) S at position 126 to F, H, L, M, Q, R, or V;
 (c) P at position 127 to A, E, L, M, N, Q, S, or Y;
 (d) S at position 128 to A, G, K, P, T, or V;
 (e) S at position 160 to C, D, G, or N; and
 (f) M at position 216 to Q or S of mature PB92 protease obtained from Bacillus novo species PB92, wherein said mature PB92 protease has an amino acid sequence as shown in FIG. 4 and wherein relative to said mature PB92 protease prior to said substitution, the mutein has demonstrated (a) improved wash performance or (b) retained wash performance and improved stability against oxidizing agents.

4. The serine protease mutein according to claim 1, wherein said substitution is at amino acid 216 and is from methionine to serine.

5. The serine protease mutein according to claim 1, wherein said substitution is at amino acid 116 and is from glycine to valine.

6. The serine protease mutein according to claim 2, wherein said substitution is one set selected from the group consisting of: (G116V, S126V, P127E, S128K); (G116V, S126G, P127Q, S128I); (G116V, S126L, P127N, S128V); (G116V, S126L, P127Q, S128A); (G116V, S126R, P127S, S128P); and (G116V, S126F, P127L, S128T).

7. A serine protease mutein according to claim 1, produced by expression of a DNA sequence encoding said proteolytic enzyme in a prokaryotic host strain transformed with an expression vector comprising said DNA sequence.

8. A substantially pure serine protease mutein comprising:
a substitution of one or more of amino acid residues at a selected site corresponding to a residue position selected from the group of consisting of 126, 127 and 128 of mature PB92 protease obtained from Bacillus novo species PB92, wherein said mature PB92 protease has an amino acid sequence as shown in FIG. 4; and wherein
relative to said mature PB92 protease prior to said substitution, the mutein has demonstrated (a) improved wash performance or (b) retained wash performance and improved stability against oxidizing agents.

* * * * *